United States Patent
Kasic, II et al.

(10) Patent No.: US 11,083,446 B2
(45) Date of Patent: Aug. 10, 2021

(54) INTRALUMINAL RETRACTOR

(71) Applicant: Manual Surgical Sciences L.L.C., Minneapolis, MN (US)

(72) Inventors: James Frank Kasic, II, Boulder, CO (US); Lawrence Kronick, Hollywood, FL (US); Shawn P. Fojtik, Park City, UT (US)

(73) Assignee: Manual Surgical Sciences L.L.C., Minneapolis, MN (US)

(*) Notice: Subject to any disclaimer, the term of this patent is extended or adjusted under 35 U.S.C. 154(b) by 49 days.

(21) Appl. No.: 16/431,597

(22) Filed: Jun. 4, 2019

(65) Prior Publication Data

US 2019/0388081 A1   Dec. 26, 2019

Related U.S. Application Data

(63) Continuation of application No. 15/143,459, filed on Apr. 29, 2016, now Pat. No. 10,307,149.

(60) Provisional application No. 62/154,555, filed on Apr. 29, 2015.

(51) Int. Cl.
| | |
|---|---|
| *A61B 17/02* | (2006.01) |
| *A61B 1/005* | (2006.01) |
| *A61B 17/00* | (2006.01) |
| *A61B 18/00* | (2006.01) |

(52) U.S. Cl.
CPC ........ *A61B 17/0218* (2013.01); *A61B 1/0056* (2013.01); *A61B 2017/00314* (2013.01); *A61B 2017/00323* (2013.01); *A61B 2018/00351* (2013.01); *A61B 2018/00577* (2013.01)

(58) Field of Classification Search
CPC .............. A61B 17/0218; A61B 1/0056; A61B 2017/00314; A61B 2017/00323; A61B 2018/00351
See application file for complete search history.

(56) References Cited

U.S. PATENT DOCUMENTS

| | | | |
|---|---|---|---|
| 10,307,149 | B2 | 6/2019 | Kasic, II et al. |
| 2007/0118097 | A1 | 5/2007 | Miller |
| 2007/0225701 | A1 | 9/2007 | O'Sullivan |
| 2011/0196204 | A1 | 8/2011 | Setty et al. |
| 2014/0135913 | A1 | 5/2014 | Lichtenstein et al. |

*Primary Examiner* — Christine H Matthews
(74) *Attorney, Agent, or Firm* — Dentons Durham Jones Pinegar

(57) ABSTRACT

An intraluminal retractor includes a shapeable element formed by a series of shaping segments. The shaping segments may be associated with one another in a relaxed configuration that imparts the shapeable element with a linear, substantially linear or curvilinear shape to enable its insertion into an interior space within a subject's body. When actuated, the shaping segments may assume a contracted configuration that imparts the shapeable element with a desired shape, which may move an organ within which or against which the shapeable element is positioned, change a path of the organ and/or alter a shape of the organ. Methods for altering the locations, paths and/or shapes of organs are also disclosed.

19 Claims, 9 Drawing Sheets

INTRALUMINAL RETRACTOR

CROSS-REFERENCE TO RELATED APPLICATION

This application is a continuation of U.S. patent application Ser. No. 15/143,459, filed on Apr. 29, 2016 and titled INTRALUMINAL RETRACTOR, now U.S. Pat. No. 10,307,149 ("the '459 Application"). A claim for the benefit of priority to the Apr. 29, 2015, filing date of U.S. Provisional Patent Application No. 62/154,555, titled INTRALUMINAL RETRACTOR AND METHOD FOR USING THE SAME ("the '555 Provisional Application"), was made is pursuant to 35 U.S.C. § 119(e) in the '459 Application. The entire disclosures of the '555 Provisional Application and the '459 Application are hereby incorporated herein.

TECHNICAL FIELD

This disclosure relates generally to devices for selectively positioning or otherwise manipulating organs (e.g., hollow organs, organs adjacent to internal body cavities, etc.) within the body of a subject. A positioning device, or intraluminal retractor, according to this disclosure may include shapeable element with a shape that will position a hollow organ, such as an esophagus, in a desired manner. Systems that include intraluminal retractors are also disclosed, as are methods for positioning organs.

RELATED ART

Catheter or electrophysiology ablation is an invasive cardiac procedure that uses radio-frequency (RF) energy or cyroablation to remove faulty electrical pathways from the heart of a person—a patient—that is prone to developing cardiac arrhythmias, such as atrial fibrillation. The procedure involves advancing several flexible catheters through the patient's blood vessels, usually via the femoral vein, internal jugular vein, or subclavian vein. The catheters are advanced into the heart and an ablation technique, such as the use of radiofrequency electrical impulses, is used to induce and/or study various arrhythmias, and to ablate the abnormal tissue that is causing the arrhythmia, if deemed necessary.

Certain ablation procedures include extensive radiofrequency ablation of the left atrial posterior wall of the heart. Radiofrequency ablation in this location carries the potential risk of collateral damage to structures adjacent to the left atrial posterior wall, including the esophagus. Esophageal injury is associated with numerous co-morbidities and a high mortality rate. Studies have shown esophageal injury with mucosal changes, which are consistent with the thermal injuries that may happen during ablation procedures, occur at a rate as high as 50% after ablation procedures. Up to 26% of patients suffer from more serious necrosis and/or ulcers. The most worrisome collateral damage is an atrial esophageal fistula, estimated to occur at a rate of approximately 0.5%; however, underreporting is likely, and the true incidence is unknown and could likely be higher. While the likelihood of an atrial-esophageal fistula is low, it is almost always a lethal complication. Fistula formation is thought to occur due to conductive heat transfer to the esophagus that causes trans-mural tissue injury leading to a fistulous connection between the esophageal lumen and the left atrium, leading to sepsis, stroke and eventual death.

The point of biggest potential vulnerability for the esophagus to thermal injury from cardiac procedures is during ablation of the posterior left heart chambers, including the left atrium. This is due to its close anatomic position of the esophagus. The esophagus is often compressed between the left atrium and surrounding structures, causing the esophagus to take a flattened and ovoid shape that may contact a broad area that could span the majority of the posterior left atrial wall. This relationship makes the esophagus particularly vulnerable to thermal injury during ablation of any part of the posterior left atrial endocardium.

Unfortunately, there is no clear technique for accurately determining the precise location(s) where the esophagus contacts or is in close proximity to the left atrium or any other part of the heart and, thus, for accurately determining whether or not the esophagus will be vulnerable during an ablation procedure. This uncertainty is compounded by the fact that peristalsis and/or deglutition of the esophagus will change the anatomic relationship between an individual's left atrium and his or her esophagus during an ablation procedure.

SUMMARY

In one aspect, an intraluminal retractor is disclosed. An intraluminal retractor according to this disclosure may include a shapeable element that is configured to be placed in an internal cavity within a subject's body, such as a lumen or chamber as a hollow organ, a location next to an exterior of an organ, or any other suitable location. With the shapeable element in place within an internal cavity, it may physically alter the shape and/or location of at least a portion of at least one organ within the subject's body. Without limitation, the shapeable element may be capable of placement within a lumen within a hollow organ (e.g., an esophagus, a portion of an intestine, a vessel, a duct, a tube, etc.) in the body of a subject, such as a patient undergoing a medical procedure (e.g., a left atrial ablation procedure, etc.), and of moving a portion of the hollow organ during the medical procedure.

An intraluminal retractor according to this disclosure includes a shapeable element and an actuator. The shapeable element may be an elongated solid element that comprises at least one series or sequence of shaping segments. The shaping segments, which are solid, may be oriented in a manner that will ultimately impart the elongated element with a desired configuration, such as a bend and a divergent section that can move the location of the hollow organ in a desired manner (e.g., move the esophagus a suitable distance away from the left atrium of the heart, maintain the diversion of the esophagus for a sufficient length, etc.). Depending upon the specific configurations of the shaping segments, the orientations of the shaping segments may impart the shapeable element with a desired two-dimensional configuration or with a desired three-dimensional configuration.

The shapeable element may have a relaxed configuration, in which it may have a shape (e.g., linear, substantially linear, curvilinear, etc.) that will facilitate its introduction into the lumen of a hollow organ. Once the shapeable element is at a desired location within the interior of the hollow organ, the actuator may be used to force it into a compressed configuration, in which it assumes its desired shape to provide a desired result, such as diverting a path of the hollow organ.

The actuator may include one or more flexible elongated elements, such as wires, cables, cords, or the like, that enable an individual, such as a health care provider, to place the shapeable element in its relaxed configuration or in its contracted configuration. In such an embodiment, each of the shaping segments of the shapeable element of the intraluminal retractor may include at least one passage or channel for receiving a portion of the elongated element. When the elongated element(s) is (are) actuated (e.g., pulled to increase tension therein, etc.), the shaping segments are forced together in an end-to-end relation to place the shapeable element in its contracted configuration. Conversely, tension in the elongated element(s) may be reduced to enable the shapeable element to return to its relaxed configuration. Of course, intermediate configurations are also possible.

In a specific embodiment the shaping segments may resemble beads. At least some of the shaping segments include at least one end with a configuration that, when that end abuts an end of an adjacent shaping segment, enables the adjacent shaping segments to be oriented at an angle of less than 180° to one another. In some embodiments, the configurations of the opposed ends of adjacent shaping segments may enable the adjacent shaping segments to be oriented at two or more different angles (e.g., 180° and an angle of less than 180°, etc.) to one another, depending upon the relative orientations of the shaping segments. The shapes that the shapeable element can assume depend on the various configurations of the ends of adjacent shaping segments. For example, a desired curvature may be achieved by having a relative angle between the opposed ends of two adjacent shaping segments. Any number of desired angles and, thus, curvatures can be achieved. In regions where no curvature is desired, the opposed ends of adjacent shaping segments may be oriented perpendicular to the lengths of the adjacent shaping segments so the adjacent shaping segments form an angle of 180° under actuation.

In another specific embodiment, adjacent shaping segments may be hingedly secured to one another, and variations in the tension in one or more flexible elongated elements of an actuator may change the shape of the shapeable element.

According to another aspect, this disclosure relates to methods for altering the position, orientation and/or shape of one or more organs within the body of a subject. In use, a shapeable element of an intraluminal retractor, while in its relaxed configuration, may be introduced into the body of a subject, and into an interior of a hollow organ or into an internal cavity of the body. In some embodiments, the shapeable element may be placed at a particular location and in a particular orientation within the hollow organ or internal cavity. Once the shapeable element is in place within the hollow organ or internal cavity, it may be moved at least partially into its contracted configuration. Contraction of the shapeable element may at least partially place it in its desired shape, which may, in turn, move, stretch or otherwise manipulate some or all of the hollow organ or internal cavity. With an organ moved or otherwise manipulated in a desired manner, other procedures may be performed. After those procedures are complete, the shapeable element may be returned to its relaxed configuration, which may reverse movement other manipulation of part or all of the organ. The shapeable element may then be removed from the hollow organ or internal cavity, and the shapeable element and the positioning device may be removed from the body of the subject.

Other aspects, as well as features and advantages of various aspects, of the disclosed subject matter will become apparent to those of ordinary skill in the art through consideration of the ensuing description, the accompanying drawings and the appended claims.

DETAILED DESCRIPTION

Figure 1A:
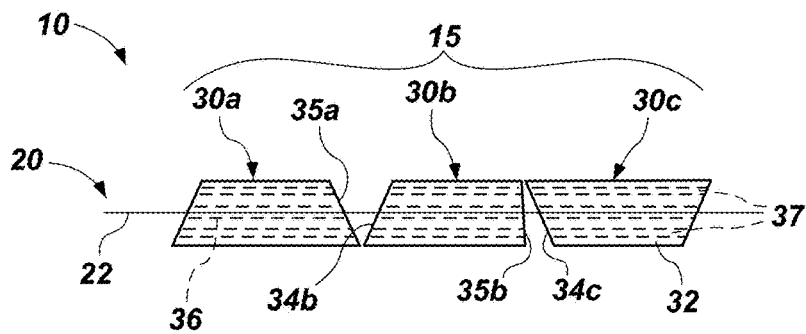
FIG. 1A schematically depicts an embodiment of an intraluminal retractor in a relaxed configuration, in which a shapeable element of the intraluminal retractor may be straight.
Figure 1B:
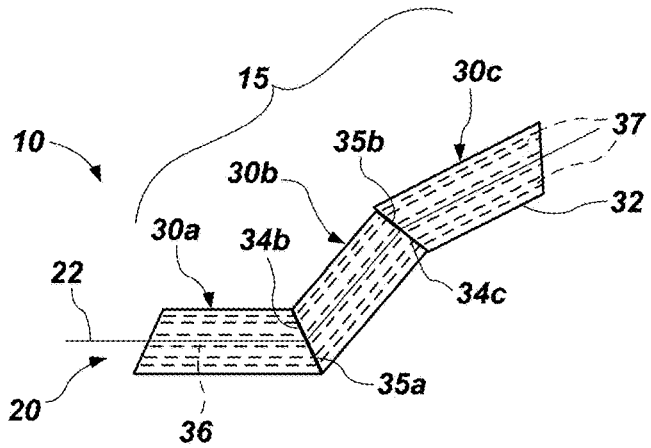
FIG. 1B schematically depicts the embodiment of intraluminal retractor shown in FIG. 1A in a contracted configuration, in which the shapeable element may be bent or curved.
Figure 1C:
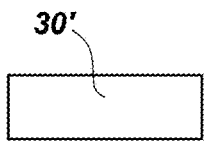
FIGS. 1C-1F illustrate various embodiments of shaping segments that may be used to form the shapeable element of an intraluminal retractor.

FIGS. 1A and 1B illustrate an embodiment of a portion of an intraluminal retractor 10 that includes an actuator 20 and an elongated shapeable element 15 made up of a plurality of shaping segments 30a, 30b, 30c, etc. The actuator 20 comprises a flexible, elongated element 22, such as a wire (e.g., a metallic wire, a polymeric wire, etc.), a cable or a cord. Each shaping segment 30a, 30b, 30c, etc., of the shapeable element 15 resides on the elongated element 22 of the actuator 20 and is positioned along a portion of a length of the elongated element 22.

Each shaping segment 30a, 30b, 30c, etc., includes a body 32 with two ends 34 and 35 (shown as ends 34b, 34c and 35a, 35b). At least one channel 36 extends through the body 32 of the shaping segment 30a, 30b, 30c, etc., from one end 34a, 34b, 34c, etc., respectively, to the other end 35a, 35b, 35c, etc., respectively.

In addition, one or more additional lumens 37 may extend through the body 32 of each shaping segment 30a, 30b, 30c, etc., to accommodate wires or other elongated medical instruments (e.g., catheters, tubes, etc.). Without limitation, an additional lumen 37 may receive a guide wire to enable insertion of the shapeable element 15 into a cavity while the shapeable element 15 is in a relaxed configuration and/or has a linear, substantially linear or curvilinear shape. An additional lumen 37 may also receive a guide wire to enable rotation of the shapeable element 15 once it is in place within the cavity within the subject's body, which may enable a user (e.g., a healthcare professional, etc.) to adjust an orientation of the shapeable element 15 while it is in its contracted configuration.

The channel 36 of each shaping segment 30a, 30b, 30c, etc., receives a portion of the elongated element 22 of the actuator 20, enabling the shaping segment 30a, 30b, 30c, etc., to reside on the elongated element 22. At least some of the shaping segments 30a, 30b, 30c, etc., may be strung on the elongated element 22 by threading the elongated element 22 into and through the channels 36 of various shaping segments 30a, 30b, 30c, etc.

Figure 2A:
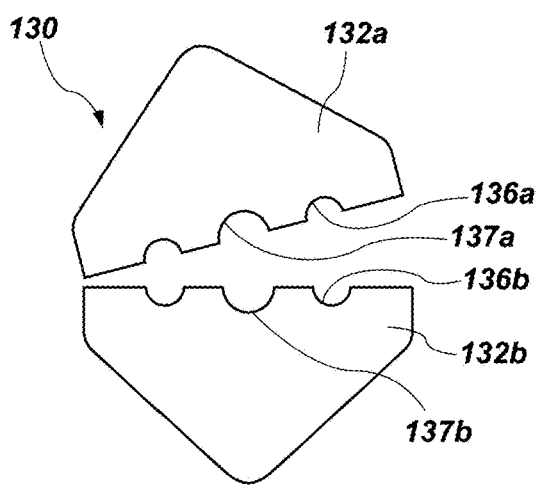
FIGS. 2A-2C depict an embodiment of a shaping segment that may assembled around an elongated element of an actuator of an intraluminal retractor.
Figure 2B:
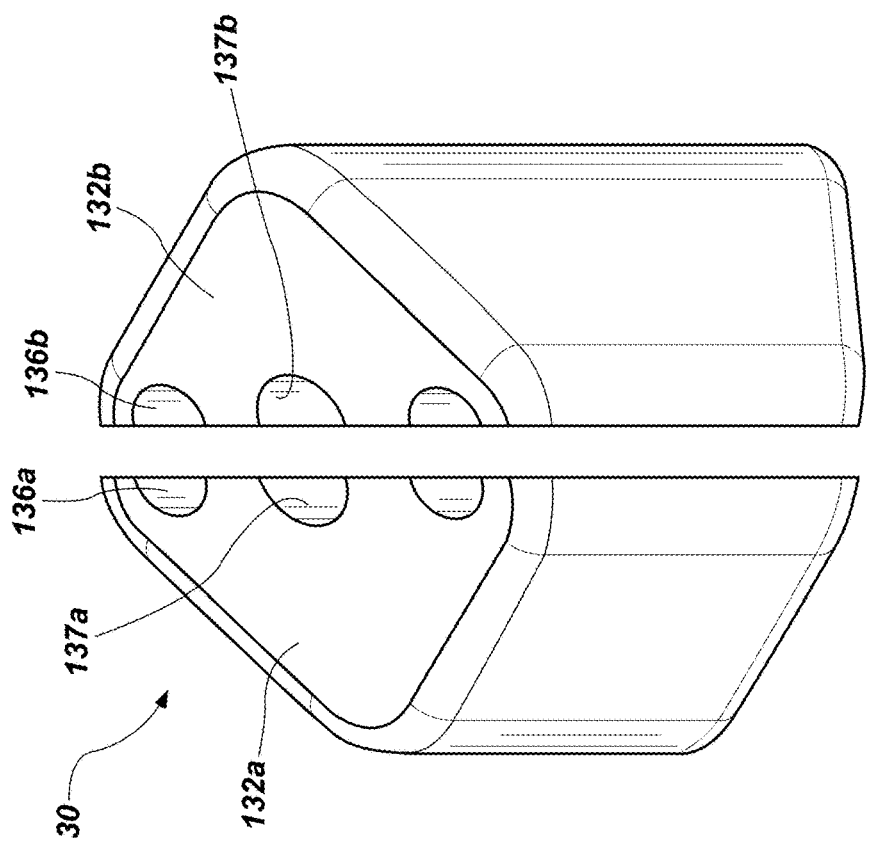
Figure 2C:
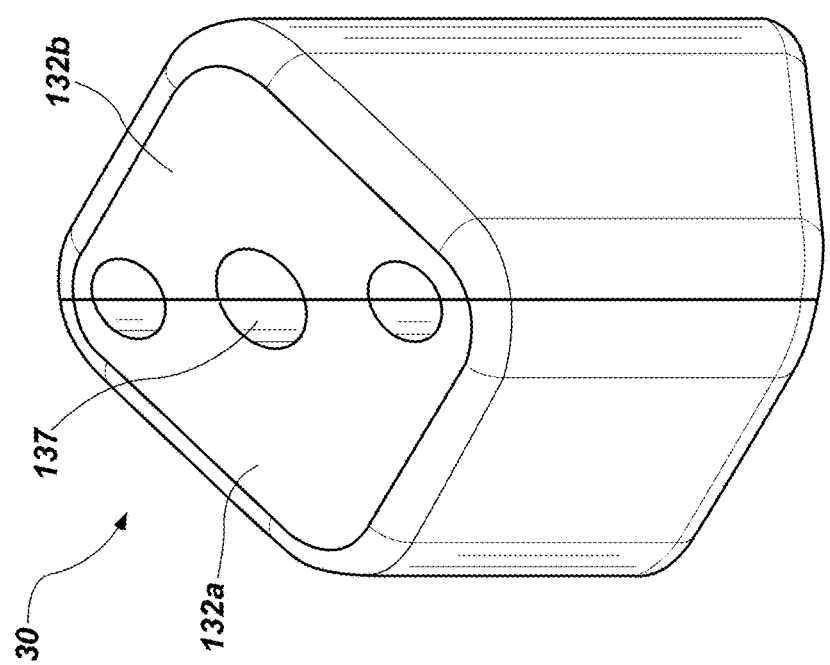

Optionally, as shown in FIGS. 2A-2C, a shaping segment 130 may have a so-called "clam shell" type configuration, in which two halves 132a and 132b of the body 132 of the shaping segment 130 define corresponding halves 136a and 136b of the channel 136 of the shaping segment 130. When the halves 132a and 132b of the body 132 of the shaping segment 130 are at least partially separated from one another (they may, for example, be connected along one edge by a hinge, such as a living hinge, etc.), a portion of an elongated element 22 (FIGS. 1A and 1B) may be inserted into a half 136a, 136b of the channel 136. As the halves 132a and 132b are assembled with one another, the halves 136a and 136b of the channel 136 define a complete channel 136 and the portion of the elongated element 22 within half 136a, 136b of the channel 136 may also be received by and captured within the other half 136b, 136a of the channel 136. Optionally, when the halves 132a and 132b of the shaping segment 130 are assembled with one another, two halves 137a and 137b of one or more lumens 137 may define a complete lumen 137.

The channel 36 may receive a portion of the elongated element 22 in a manner that enables rotation of the shaping segment 30a, 30b, 30c, etc., about the portion of the elongated element 22. In some embodiments, the shaping segment 30a, 30b, 30c, etc., may be rotated about the portion of the elongated element 22 to position it in an infinite number of orientations relative to the elongated element 22 and relative to one or more other shaping segments 30a, 30b, 30c, etc., that are carried by the elongated element 22. In other embodiments, the shaping segment 30a, 30b, 30c, etc., may be positioned in a fixed number of positions, or orientations, about the elongated element 22 (e.g., incremental positions, etc., which may be defined by discrete longitudinal surfaces of the elongated element 22, longitudinal grooves at different locations around the circumference or perimeter of the elongated element, longitudinal protrusions at different locations around the circumference or perimeter of the elongated element, etc.).

FIG. 1A shows the shaping segments 30a, 30b, 30c, etc., and the intraluminal retractor 10 in a relaxed configuration, in which adjacent shaping segments 30a and 30b, 30b and 30c, etc., are at least partially spaced apart from one another and in which the elongated element 22 of the actuator 20 may be linear or substantially linear. In the relaxed configuration, there may be little or no tension in the elongated element 22.

A distal end of the elongated element 22 may be secured in place relative to the distal-most shaping segment 30n of the shapeable element 15. Tension may be introduced into the elongated element 22 by pulling the elongated element 22 proximally with an actuation feature (not shown in FIG. 1A or FIG. 1B) of the actuator 20, which may be manually operated. The actuation feature may lock into place to maintain a desired amount of tension in the elongated element 22.

With tension in the elongated element 22 of the actuator 20, as shown in FIG. 1B, ends 35a and 34b, 35b and 34c, etc., of adjacent shaping segments 30a and 30b, 30b and 30c, etc., respectively, have been forced against each other, placing the shaping segments 30a, 30b, 30c, etc., and the intraluminal retractor 10 in a contracted configuration. With the intraluminal retractor 10 in the contracted configuration, the elongated element 22 assumes a shape defined by the configurations of the opposed, abutting ends 35a and 34b, 35b and 34c, etc., of adjacent shaping segments 30a and 30b, 30b and 30c, etc., respectively, and the orientations of the adjacent shaping segments 30a and 30b, 30b and 30c, etc. Depending upon the relative orientations of the adjacent shaping segments 30a and 30b, 30b and 30c, etc., and the opposed, abutting ends 35a and 34b, 35b and 34c, etc., of the adjacent shaping segments 30a and 30b, 30b and 30c, etc., the intraluminal retractor 10 may assume a linear configuration or any of a plurality of different non-linear configurations, such as the non-linear configuration depicted by FIG. 1B.

Figure 1D:
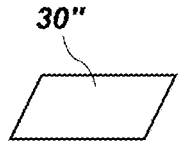
Figure 1E:
Figure 1F:
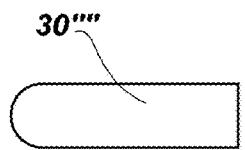

Shaping segments 30a and 30c shown in FIGS. 1A and 1B include flat ends 34a, 35a and 34c, 35c, respectively, that are oriented oblique relative to the channels 36 of the shaping segments 30a and 30c and non-parallel to one another. Shaping segment 30b, which is also shown in FIGS. 1A and 1B, includes one flat end 34b that is oriented oblique relative to the channel 36 of that shaping segment 30b and another flat end 35b that is oriented perpendicular to the channel 36 of that shaping segment 30b. Other embodiments of shaping segments 30', 30", 30"' and 30"" are shown in FIGS. 1C-1F, respectively. The embodiment of shaping segment 30' shown in FIG. 1C includes flat ends 34' and 35' that are both oriented perpendicular to the channel 36' of that shaping segment 30'. FIG. 1D illustrates an embodiment of a shaping segment 30" with flat ends 34" and 35" that have oblique orientations relative to the channel 36" of that shaping segment 30", with the flat ends 34" and 35" being oriented parallel to each other. In FIG. 1E, an embodiment of a shaping segment 30"' that includes at least one convex end 34"' and/or at least one concave end 35"' (e.g., one convex end 34"' and one concave end 35"', two convex ends, two concave ends, etc.). FIG. 1F shows another embodiment of shaping segment 30"", which may include at least one end 34''' with two flat surfaces that form a convex taper and/or at least one end 35''' with two flat surfaces that form a concave taper.

Figure 8:
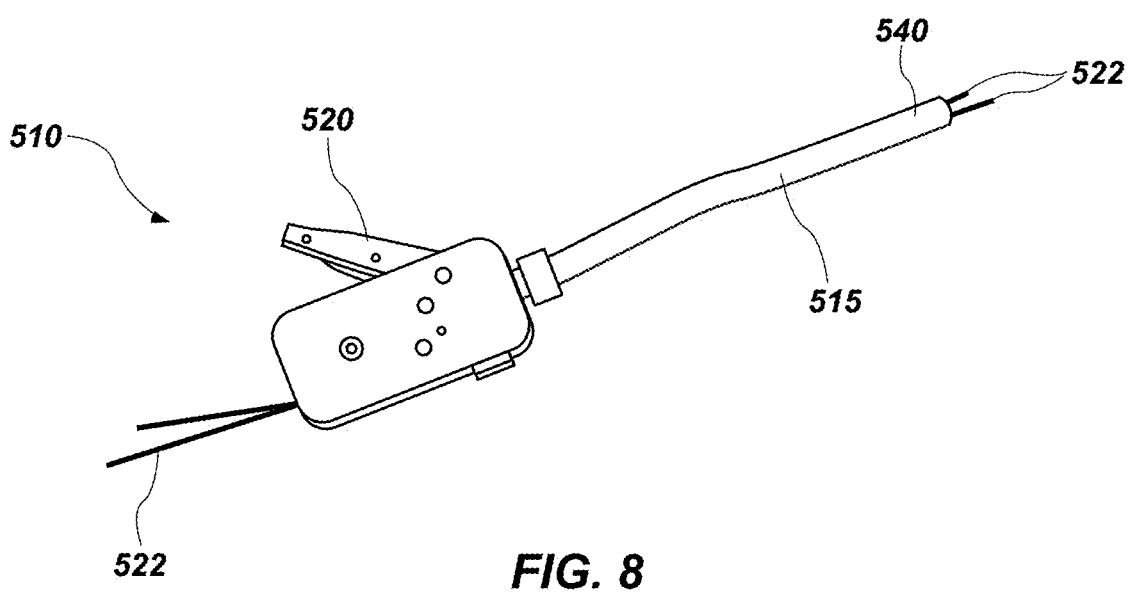
FIG. 8 illustrates an embodiment of an intraluminal retractor with its shapeable element in a relaxed configuration.
Figure 13:
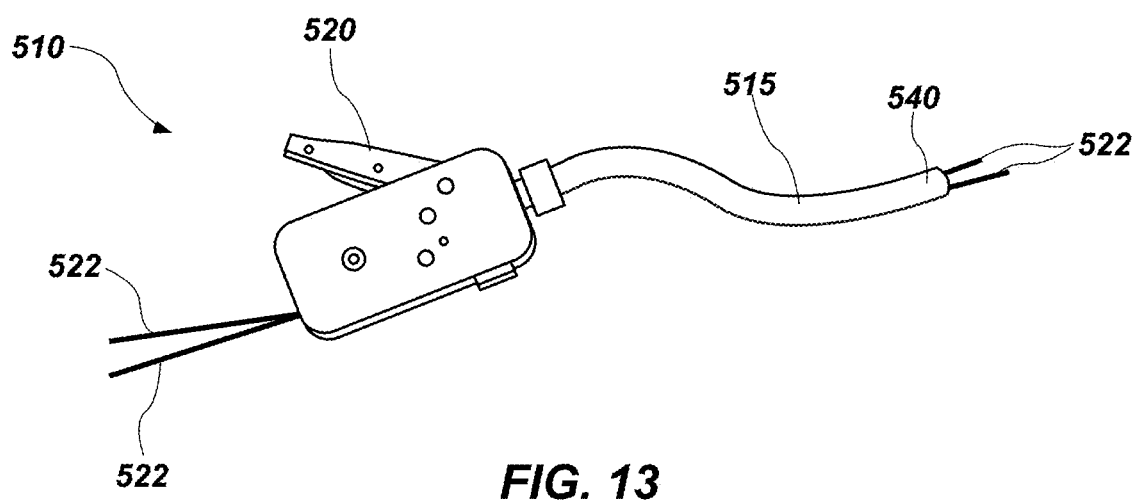
FIG. 13 illustrates the embodiment of intraluminal retractor shown in FIG. 8 with its shapeable element in a contracted configuration.

With returned reference to FIG. 1B, when the adjacent ends 35a and 34b, 35b and 34c, etc., of adjacent shaping segments 30a and 30b, 30b and 30c, etc., are forced together (e.g., increasing tension in the elongated element 22 of the actuator 20; see, e.g., FIGS. 8 and 13), the relative orientations of the shaping segments 30a, 30b, 30c, etc., and the adjacent ends 35a and 34b, 35b and 34c, etc., may impart the intraluminal retractor 10 with a desired shape. As illustrated by FIG. 1B, the shaping segments 30a, 30b, 30c, etc., may be oriented about the elongated element 22 of the actuator 20 in a manner that imparts the intraluminal retractor 10 with a non-linear configuration or shape. That non-linear configuration or shape may comprise a two-dimensional diversion or a three-dimensional diversion that may alter the path of an elongated hollow organ (e.g., the esophagus, a portion of an intestine, a vessel, a duct, a tube, etc.) when the intraluminal retractor 10 is positioned within the elongated hollow organ and assumes a non-linear configuration or shape as it is placed in its contracted configuration within the elongated hollow organ.

As an alternative to an intraluminal retractor 10 that assumes a desired shape when an actuator 20 increases tension within the elongated element 22 to pull the shaping segments 30a, 30b, 30c, etc., together (e.g., by pulling the distal-most shaping segment proximally, etc.), adjacent shaping segments 30a, 30b, 30c, etc., may impart the intraluminal retractor 10 with a desired configuration when they are oriented relative to one another. For example, the opposed, or facing, ends 35a and 34b, 35b and 34c, etc., of adjacent shaping segments 30a and 30b, 30b and 30c, etc., may be secured to one another as the adjacent shaping segments 30a and 30b, 30b and 30c, etc., are placed in their desired orientations. This may be accomplished in any of a variety of ways; for example, by use of tongue and groove connections (which would limit each adjacent pair of adjacent shaping segments 30a and 30b, 30b and 30c, etc., to two relative orientations and could be used to restrict the contracted configuration to a two-dimensional configuration, or bend), by use of a snap fit (which could provide for three or more discrete orientations between each pair of adjacent shaping segments 30a and 30b, 30b and 30c, etc., and provide for three-dimensional arrangements, depending upon the shapes of the cooperating snap elements) or in any other suitable manner.

While FIG. 1B illustrates an intraluminal retractor 10 that assumes a particular two-dimensional shape when its shaping segments 30a, 30b, 30c, etc., are placed in the depicted orientation and compressed together, it should be apparent that a variety of other shapes or configurations may be achieved by placing one or more of the shaping segments 30a, 30b, 30c, etc., in a different orientation, by using a different arrangements of shaping segments and/or by using shaping segments 30', 30'', 30''' of different configurations. Customization or tailoring of the intraluminal retractor 10 may be achieved in part in the order in which shaping segments 30a, 30b, 30c, etc., as well as any shaping segments 30', 30'', 30''', are placed along the length of the elongated element 22 of the actuator 20.

Figure 3A:
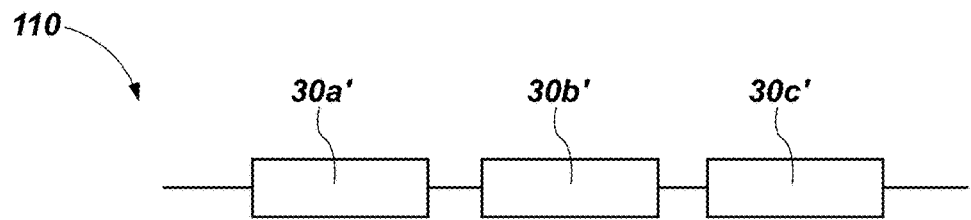
FIG. 3A schematically depicts an embodiment of an intraluminal retractor with a nominal configuration.
Figure 3B:
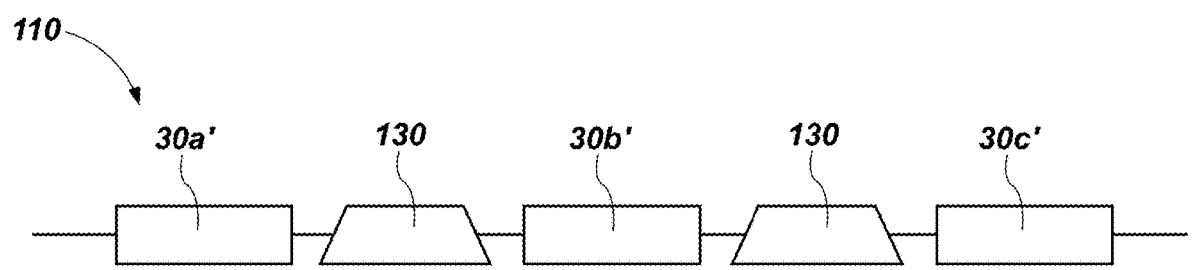
FIG. 3B schematically depicts an embodiment of the intraluminal retractor of FIG. 3A that has been customized by the addition of shaping segments with non-nominal shapes to enable a shapeable element of the intraluminal retractor to be bent or curved in a desired manner.

Configurations of shaping segments 130 that may be placed on an elongated element 22 without requiring that the elongated element 22 be threaded through their channels 136, such as the configuration of shaping segments 130 shown in FIGS. 2A-2C, may facilitate such customization and/or tailoring of an intraluminal retractor 110 (FIGS. 3A and 3B). In addition, the use of shaping segments 130 with such configurations may increase the speed with which (or decrease the time required to) customize or tailor an intraluminal retractor 10. As illustrated by FIGS. 3A and 3B, an intraluminal retractor 110 with a nominal configuration in which all of the shaping segments 30a', 30b', 30c', etc., have the same shape (e.g., that of the shaping segment 30' depicted by FIG. 1C, etc.) may be tailored by introducing shaping segments 130 (FIGS. 2A-2C) with one or more different shapes (e.g., that of the shaping segment 30a shown in FIGS. 1A and 1B) between adjacent shaping segments 30a' and 30b', 30b' and 30c', etc.

Various examples of possible configurations for an intraluminal retractor 10 according to this disclosure are depicted by FIGS. 4A-7.

Figures 4A, 4B:
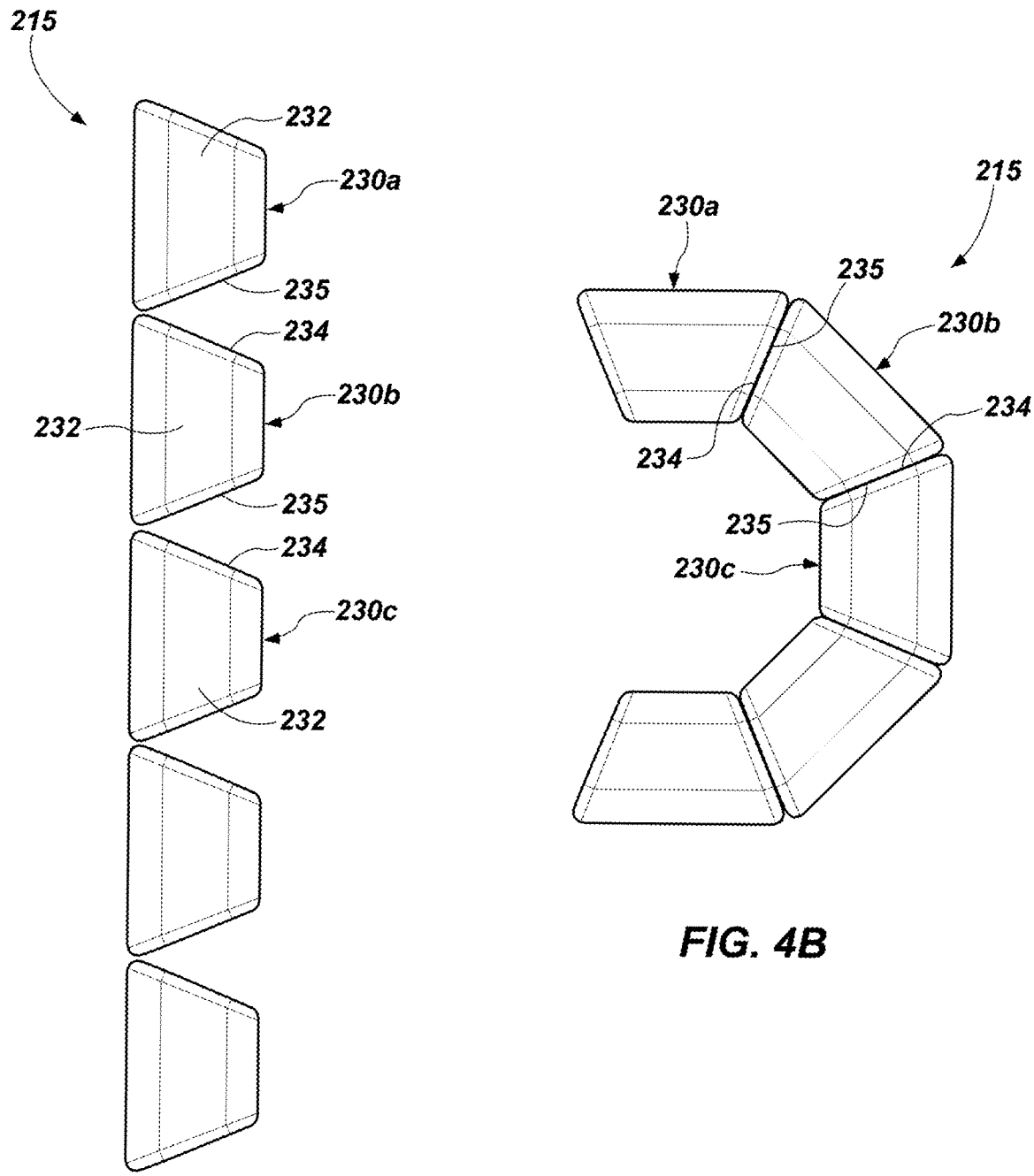
FIG. 4A illustrates an embodiment of a shapeable element with its shaping segments in a relaxed configuration.
FIG. 4B illustrates the embodiment of shapeable element shown in FIG. 4A with its shaping segments in a contracted configuration.
Figure 4C:
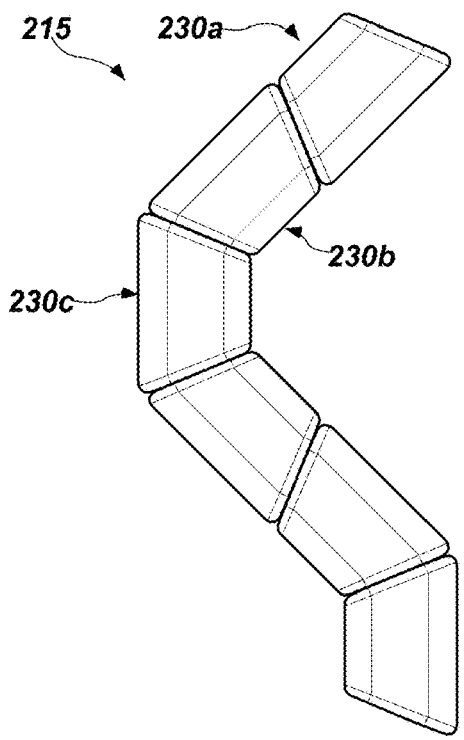
FIG. 4C illustrates the embodiment of shapeable element shown in FIG. 4A with the orientations of some of its shaping segments having been rotated, and placed in a contracted configuration that imparts the shapeable element with a different shape than that illustrated by FIG. 4B.

FIG. 4A illustrates an embodiment of a shapeable element 215 for an intraluminal retractor. The shapeable element 215 includes a plurality of shaping segments 230a, 230b, 230c, etc., that have the same configurations as shaping segments 30a and 30c of the intraluminal retractor 10 shown in FIGS. 1A and 1B. More specifically, each shaping segment 230a, 230b, 230c, etc., includes a body 232 with two ends 234 and 235 that are oriented obliquely relative to a channel 236 extending through the body 232. The ends 234 and 235 of the body 232 are also oriented non-parallel to one another, imparting the body 232 and each shaping segment 230a, 230b, 230c, etc., with a trapezoidal shape. When the shaping segments 230a, 230b, 230c, etc., of the shapeable element 215 are oriented in the same direction, as shown in FIG. 4A, and then forced against one another, or compressed, they assume the contracted configuration shown in FIG. 4B. FIG. 4C shows an alternative compressed configuration that may be used to enable the physical diversion of a portion of an elongated hollow organ.

Figure 5:
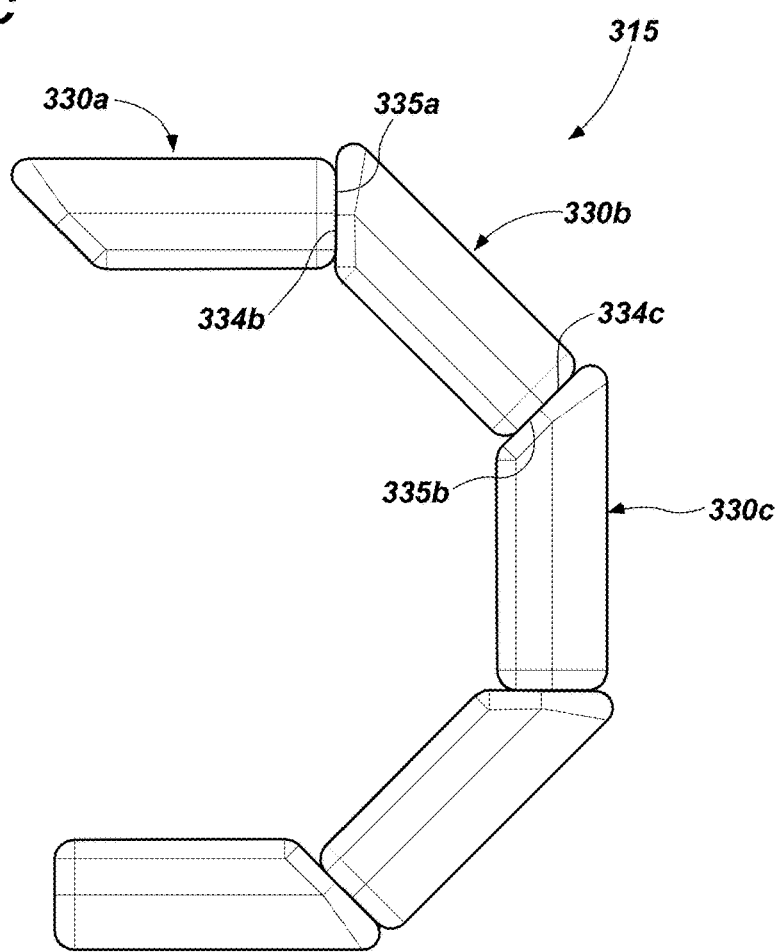
FIG. 5 depicts another embodiment of shapeable element, with its shaping segments in a contracted configuration.

In FIG. 5, an embodiment of a shapeable element 315 is shown with shaping segments 330a, 330b, 330c, etc., that each have one end 334 that is oriented perpendicular to the length of each shaping segment 330a, 330b, 330c, etc., and another opposite end 335 with an orientation that is oblique to the length of the channel 336. When adjacent ends 335a and 334b, 335b and 334c, etc., are arranged in the same orientations about an elongated element 22 (FIGS. 1A and 1B) as one another and abut one another (e.g., are forced against each other, are secured to each other, etc.), the intraluminal retractor 310 assumes the contracted configuration shown in FIG. 5.

Figures 6, 7:
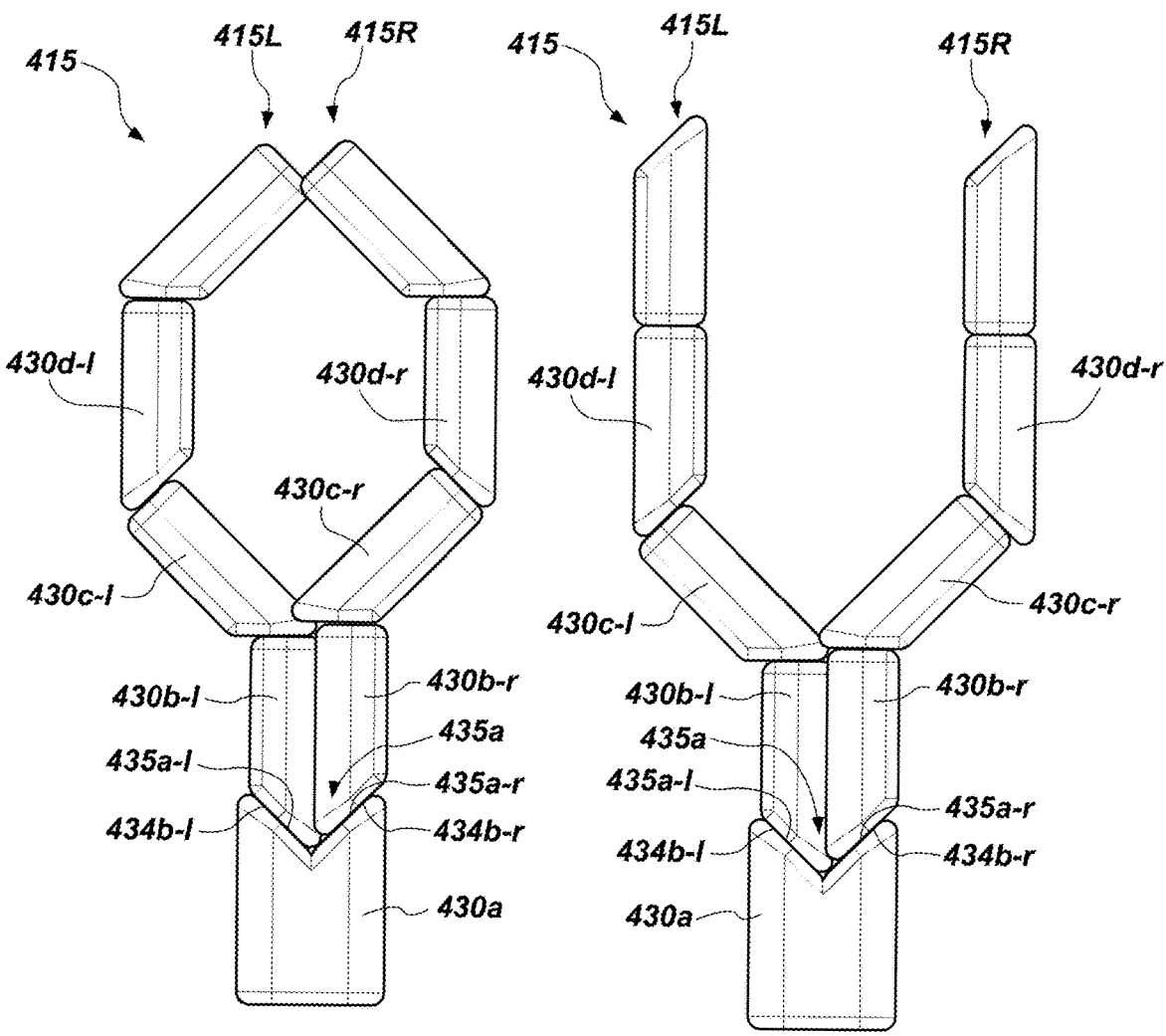
FIGS. 6 and 7 show branched embodiments of shapeable elements, with their shaping segments in different contracted configurations.

FIGS. 6 and 7 illustrate two configurations of a shapeable elements 415 with a pair of divergent sections, which are referred to as branches 415L and 415R. The shapeable element 415 includes a shaping segment 430a with an end 435a that includes two surfaces 435l and 435r that taper inwardly toward one another, or in a concave manner. Such a configuration enables the two branches 415L and 415R to diverge from the shaping segment 430, as would a shaping segment 30'''' with two flat surfaces 435a-l and 435a-r that form a convex taper, such as that shown in FIG. 1F. As illustrated, the end 435a is configured to receive two shaping segments 430b-l and 430b-r with ends 434b-l and 434b-r that are oriented obliquely to the lengths of the shaping segments 430b-l and 430b-r. The subsequent shaping segments 430c-l, 430d-l, etc., and 430c-r, 430d-r, etc., of each branch 415L and 415R may then be arranged to impart their respective branch 415L, 415R with a desired shape, such as the curved loop shown in FIG. 6 or the parallel branches 415L and 415R shown in FIG. 7.

In any of the foregoing embodiments, as well as other embodiments that incorporate teachings of this disclosure, a sleeve may cover the shapeable element (see, e.g., FIGS. 8 and 13). A sleeve may prevent the shaping segments from binding tissues against which they are positioned, particularly as the shape of the elongated shapeable element is altered while the elongated shapeable element contacts those tissues.

Figure 9:
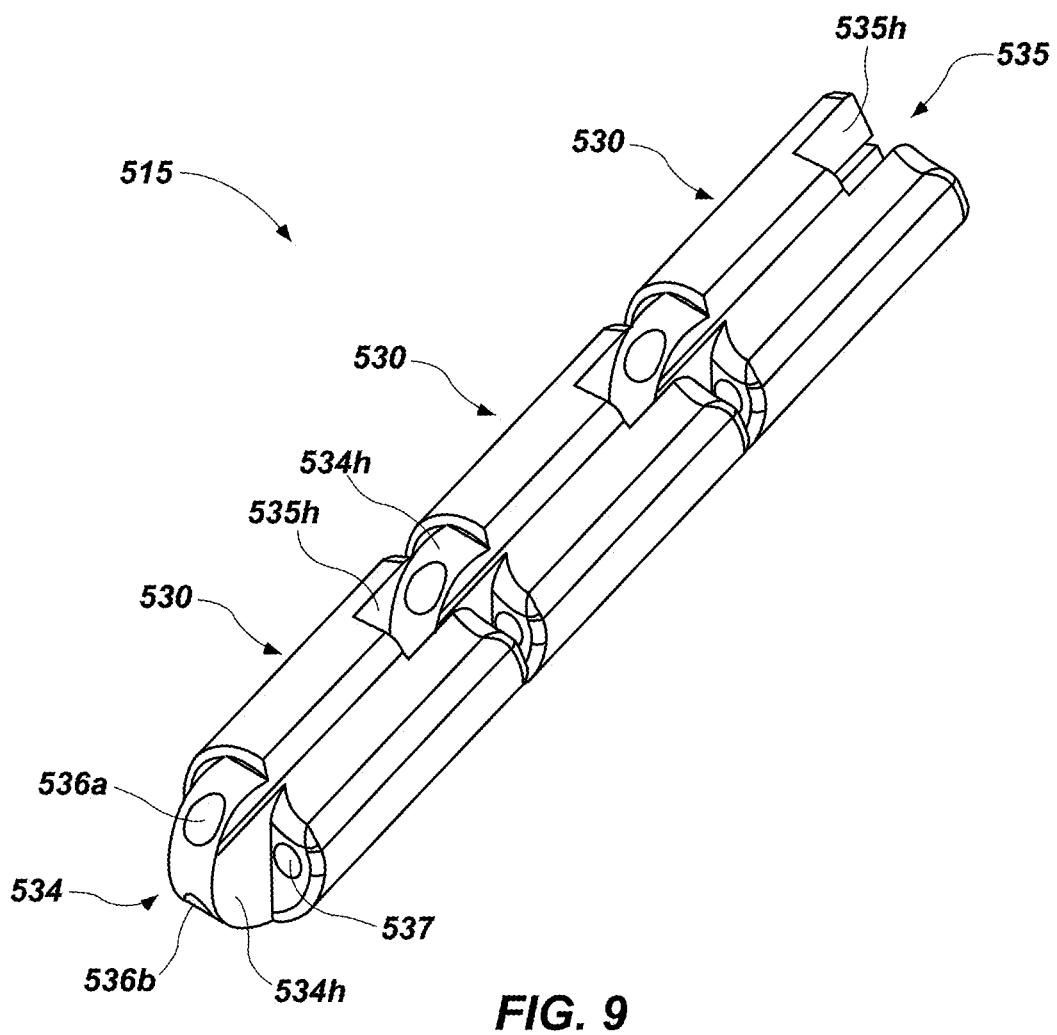
FIG. 9 depicts an embodiment of shaping segments that may form the shapeable element shown in FIG. 8, as well as an embodiment of a hinged arrangement between adjacent shaping segments, with the shapeable element and its shaping segments in a relaxed configuration.

Turning now to FIGS. 8-13, another embodiment of intraluminal retractor 510 is depicted. With specific reference to FIGS. 8 and 13, such an intraluminal retractor 510 includes an elongated shapeable element 515 and an actuator 520. The elongated shapeable element 515 is configured to be inserted into a lumen of an elongated hollow organ, such as an esophagus, a portion of an intestine, a vessel, a duct, a tube or the like. In FIGS. 8 and 13, only a sleeve 540 of the elongated shapeable element 515 is visible. The sleeve 540 covers a series of shaping segments 530 that form the shapeable element 515, an embodiment of which is depicted by FIG. 9.

In the illustrated embodiment, each shaping segment 530 includes a first end 534 with a protruding hinge element 534h and a second end 535 with a recessed hinge element 535h. The recessed hinge element 535h of each shaping segment 530 is configured to receive a corresponding protruding hinge element 534h of an adjacent shaping segment 530, which couples a pair of adjacent shaping segments 530 to one another. When a protruding hinge element 534h is properly assembled with a corresponding recessed hinge element 535h, the adjacent shaping segments 530 that have been coupled to each other may pivot relative to one another. In the depicted embodiment, each protruding hinge element 534h is rounded, and has the appearance of a semi-circular disk. Each recessed hinge element 535h comprises a narrow rectangular slot extending into the second end 535 of the shaping segment 530, across a diameter of the shaping segment 530. These and similar configurations enable pivotal movement of the protruding hinge element 534h and the recessed hinge element 535h in a single plane, or two-dimensional movement of the adjacent shaping segments 530 relative to one another; however, hinge elements that provide for a greater range of motion, or three-dimensional movement of adjacent shaping segments relative to one another, are also within the scope of this disclosure.

Figure 10:
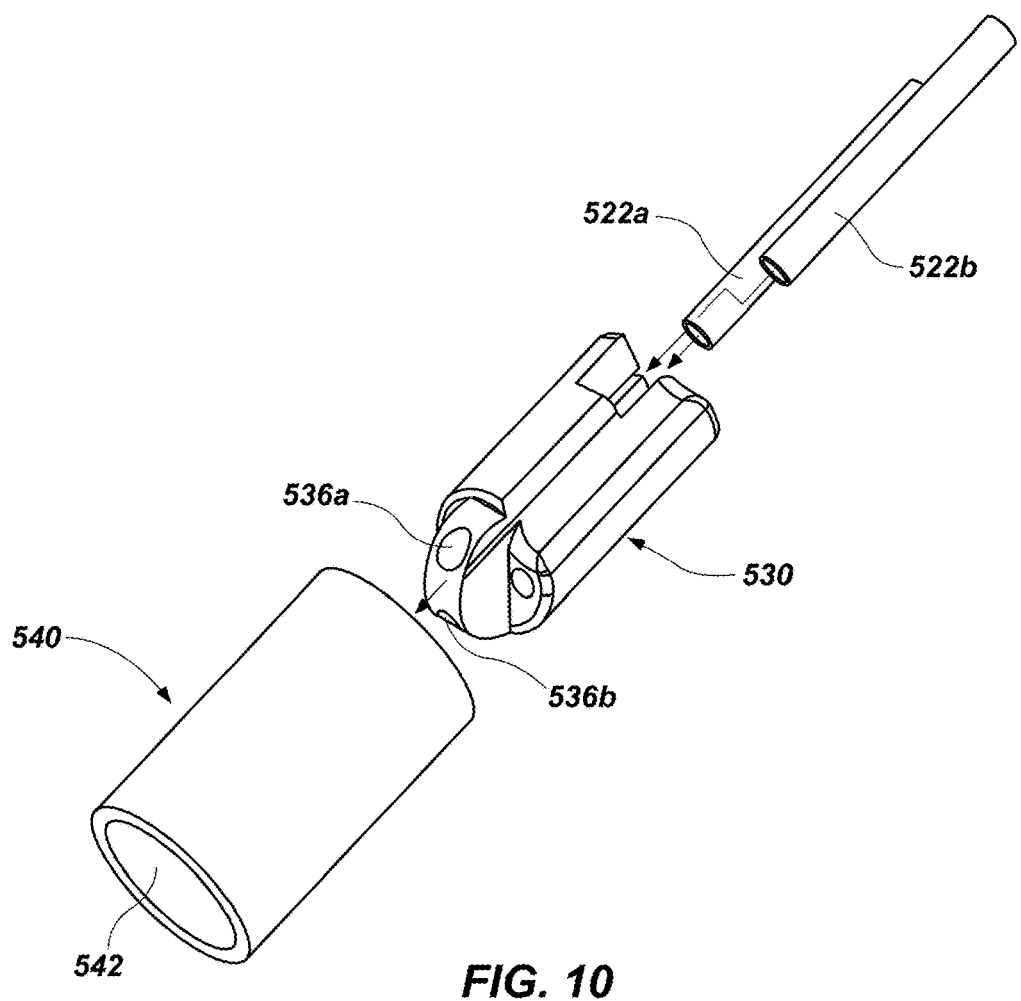
FIG. 10 is an assembly view that schematically illustrates an embodiment of a relationship between the shaping segments of the embodiment of shapeable element shown in FIG. 9 with elongated elements of an actuator of the intraluminal retractor shown in FIG. 8 and a sleeve for the shapeable element.

As illustrated by the assembly view provided by FIG. 10, a series of shaping segments 530 may reside within the lumen 542 of the sleeve 540. Such an arrangement may prevent the shaping segments 530 from binding tissues against which the elongated shapeable element 515 (FIGS. 8, 9 and 13) may be positioned (e.g., the tissues that form the inner walls of a lumen of a hollow organ, the tissues that form an outer wall of an organ within a body cavity within which the shapeable element 515 is positioned, etc.), particularly as the shape of the elongated shapeable element 515 is altered as the elongated shapeable element 515 resides against part of an organ.

FIG. 10 also shows that a pair of elongated elements 522a and 522b of the actuator 520 (FIGS. 8 and 13) may be assembled with each shaping segment 530. More specifically, each elongated element 522a, 522b may extend through a corresponding channel 536a, 536b that extends through the length of the shaping segment 530, with one end of each channel 536a, 536b opening into the recessed hinge element 535h at a corresponding end 535 of the shaping segment 530 and the other end of each channel 536a, 536b opening to an outer edge of the protruding hinge element 534h at the opposite end 534 of the shaping segment 530. More specifically, the channels 536a and 536b may be positioned close to the ends of the protruding hinge element 534h (see also FIG. 11) and of recessed hinge element 535h (FIG. 9). Such positioning may enable the elongated elements 522a and 522b to control pivotal movement of adjacent shaping segments 530 as the tension in each elongated element 522a, 522b is adjusted (e.g., increased in one elongated element 522a, 522b, relaxed in the other elongated element 522b, 522a; etc.).

Figure 12:
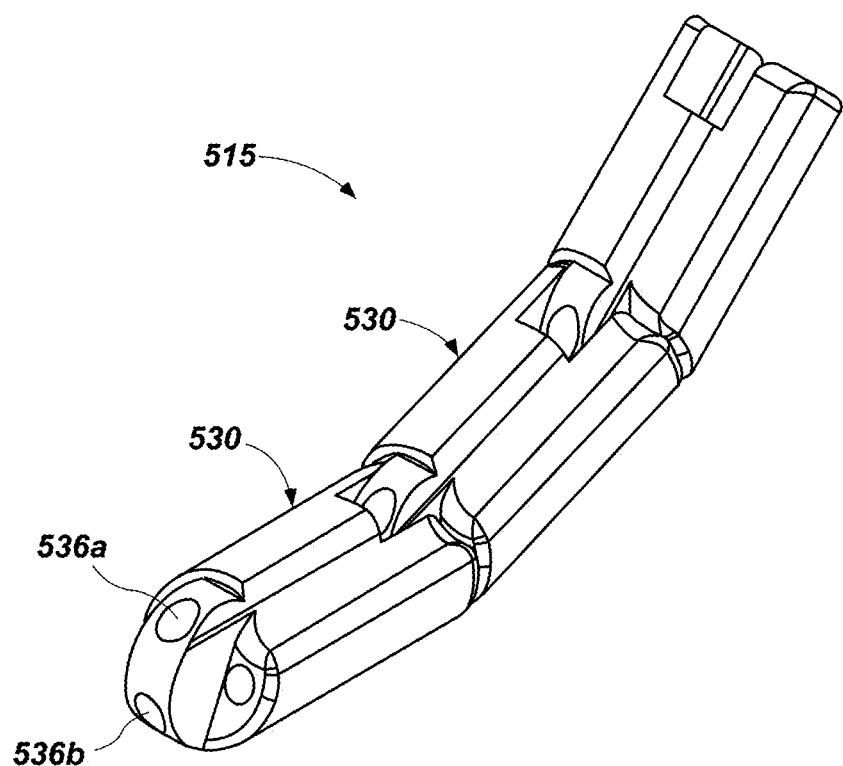
FIG. 12 depicts the embodiments of shapeable element and shaping segments shown in FIG. 9 in a contracted configuration.

As illustrated by FIGS. 9 and 12, when the tension in an elongated element 522a (FIG. 10) residing within the aligned channels 536a of a series of shaping segments 530 is increased (and, optionally, the tension in an elongated element 522b (FIG. 10) residing within the aligned channels 536b of the series of shaping segments 530 is decreased, or relaxed), the shape of the elongated shapeable element 515 may be altered. More specifically, the elongated shapeable element 515 may move from the straight configuration shown in FIG. 9 to the bent or curved configuration shown in FIG. 13.

Figure 11:
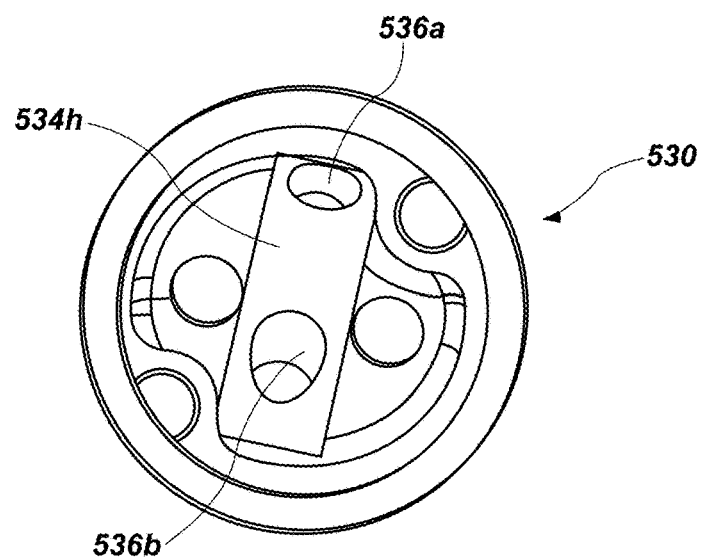
FIG. 11 provides an end view of the embodiment of shaping segment shown in FIGS. 9 and 10.

In addition, with returned reference to FIGS. 9, 11 and 12, one or more additional lumens 537 may extend through the body of each shaping segment 530 to accommodate wires (e.g., guide wires for enabling insertion of the shapeable element 15 into a cavity within a subject's body, for enabling rotation of the shapeable element 15 once it is in place within the cavity within the subject's body, etc.) or other elongated medical instruments (e.g., catheters, tubes, etc.).

While the drawings illustrate shapeable elements with specific numbers of shaping segments, it should be understood that the drawings are merely intended to provide an indication of the manner in which adjacent shaping segments may be associated with one another. A shapeable element may include any number of shaping segments that will impart the shapeable element with a desired shape. The dimensions of the shaping segments and the shapeable element may also be tailored for a particular use, or for use with a particular organ.

Although the foregoing disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

What is claimed:

1. An intraluminal retractor, comprising:
  an elongated element;
  a plurality of shaping segments on the elongated element, each shaping segment including:
    a body including a first half and a second half removably assemblable with each other over the elongated element to selectively define orientations of an adjacent pair of shaping segments of the plurality of shaping segments;
    a channel extending through a length of the body, the channel including a first half recessed in an abutting surface of the first half of the body and a second half recessed in an abutting surface of the second half of the body, the channel capable of receiving a portion of the elongated element and enabling each shaping segment to be oriented in a plurality of orientations about the portion of the elongated element; and
    ends, including a proximal end and a distal end opposite from one another; and
  an actuator that selectively enables:
    placement of adjacent shaping segments of the plurality of shaping segments in a relaxed state; or forcing the adjacent shaping segments against one another to place and/or hold the intraluminal retractor in a retracted state, orientations of adjacent shaping segments of the plurality of shaping segments about the actuator defining a shape of the intraluminal retractor while in the retracted state.

2. The intraluminal retractor of claim 1, wherein at least one end of the ends of at least one shaping segment of the plurality of shaping segments comprises a flat surface oriented perpendicular to a length of the channel through the at least one shaping segment.

3. The intraluminal retractor of claim 2, wherein the ends of the at least one shaping segment comprise flat surfaces oriented perpendicular to the length of the channel through the at least one shaping segment.

4. The intraluminal retractor of claim 1, wherein at least one end of the ends of at least one shaping segment of the plurality of shaping segments comprises a flat surface oriented obliquely to a length of the channel through the at least one shaping segment.

5. The intraluminal retractor of claim 4, wherein the ends of the at least one shaping segment comprise flat surfaces oriented obliquely to the length of the channel through the at least one shaping segment.

6. The intraluminal retractor of claim 5, wherein the flat surfaces of the ends of the at least one shaping segment are oriented parallel to one another.

7. The intraluminal retractor of claim 5, wherein the flat surfaces of the ends of the at least one shaping segment are oriented non-parallel to one another.

8. The intraluminal retractor of claim 7, wherein the flat surfaces of the ends of every shaping segment of the plurality of shaping segments are oriented non-parallel to one another.

9. The intraluminal retractor of claim 1, wherein a first end of the ends of at least one shaping segment of the plurality of shaping segments comprises a convex surface.

10. The intraluminal retractor of claim 9, wherein a second end of the ends of another shaping segment of the plurality of shaping segments adjacent to the first end of the at least one shaping segment comprises a concave surface capable of mating in a plurality of orientations with the convex surface of the first end of the at least one shaping segment.

11. An intraluminal retractor, comprising:
an elongated element;
a plurality of shaping segments positioned sequentially along a length of the elongated element, each shaping segment removable from and replaceable on the elongated element and including:
a body including a first half and a second half capable of being assembled with each other over the elongated element to define an orientation of each shaping segment relative to an orientation of at least one adjacent shaping segment;
a channel extending through a length of the body, the channel including a first half recessed in an abutting surface of the first half of the body and a second half recessed in an abutting surface of the second half of the body, the channel capable of receiving a portion of the elongated element and enabling each shaping segment to be oriented in a plurality of orientations about the portion of the elongated element; and
ends, including a proximal end and a distal end opposite from one another, the intraluminal retractor having a relaxed state in which positions of adjacent shaping segments of the plurality of shaping segments are able to change relative to one another,
the intraluminal retractor having a retracted state in which the plurality of shaping segments is rigid, positions of adjacent shaping segments of the plurality of shaping segments being substantially fixed relative to one another.

12. The intraluminal retractor of claim 11, wherein at least one end of the ends of at least one shaping segment of the plurality of shaping segments comprises a flat surface oriented perpendicular to a length of the channel through the at least one shaping segment.

13. The intraluminal retractor of claim 11, wherein the ends of at least one shaping segment of the plurality of shaping segments comprise flat surfaces oriented obliquely to a length of the channel through the at least one shaping segment.

14. The intraluminal retractor of claim 13, wherein the flat surfaces of the ends of the at least one shaping segment are oriented non-parallel to one another.

15. A method for moving a portion of an esophagus away from a left atrium of a heart, comprising:
assembling a plurality of shaping segments with an elongated element in orientations to define a shapeable element that will deflect the esophagus in a desired manner, including:
orienting a first member of each shaping segment in a desired position along the elongated element and relative to at least one adjacent shaping segment of the plurality of shaping segments;
introducing a portion of the elongated element into a portion of a channel recessed within an abutting surface of the first member of each shaping segment; and
securing a second member of each shaping segment over the abutting surface of the first member, with the portion of the elongated element within the channel recessed within the abutting surface of the first member;
inserting the shapeable element into the esophagus while the shapeable element is in a relaxed state; and
introducing tension into the shapeable element to bring the shapeable element into a retracted state to deflect the portion of the esophagus away from the left atrium of the heart without distending the esophagus.

16. The method of claim 15, further comprising:
conducting a procedure on the left atrium of the heart with the portion of the esophagus deflected away from the left atrium of the heart.

17. The method of claim 16, wherein conducting the procedure comprises conducting an atrial ablation procedure.

18. The method of claim 15, further comprising:
changing at least one of a position, an orientation, and a configuration of the shapeable element within the portion of the esophagus.

19. The method of claim 15, further comprising:
placing the shapeable element back in the relaxed configuration; and
with the shapeable element in the relaxed configuration, removing the shapeable element from the esophagus.

* * * * *